United States Patent [19]

Nishikibe et al.

[11] Patent Number: 5,494,923
[45] Date of Patent: Feb. 27, 1996

[54] METHOD OF AMELIORATING CEREBRAL CIRCULATION

[75] Inventors: Masaru Nishikibe, Urayasu; Kazuo Kamei, Fuchu; Jun Nagura, Ichikawa; Takahiro Fukuroda, Tokyo, all of Japan

[73] Assignee: Banyu Pharmaceutical Co., Ltd., Tokyo, Japan

[21] Appl. No.: 409,669

[22] Filed: Mar. 24, 1995

Related U.S. Application Data

[62] Division of Ser. No. 282,657, Jul. 29, 1994, Pat. No. 5,444,077, which is a continuation of Ser. No. 645,309, Jan. 24, 1991, abandoned, which is a continuation of Ser. No. 254,106, Oct. 6, 1988, abandoned.

[30] Foreign Application Priority Data

Oct. 6, 1987 [JP] Japan .................................. 62-251988
Feb. 26, 1988 [JP] Japan .................................. 63-43526

[51] Int. Cl.$^6$ ........................................ A81K 31/44
[52] U.S. Cl. .............................................. 514/356
[58] Field of Search ............................ 514/356; 546/321

[56] References Cited

FOREIGN PATENT DOCUMENTS 152373  8/1984  Japan .

OTHER PUBLICATIONS

Nagura et al, Japan, J. Pharmacol., vol. 40 (1986) pp. 399–409.

Primary Examiner—Richard L. Raymond
Attorney, Agent, or Firm—Oblon, Spivak, McClelland, Maier, & Neustadt

[57] ABSTRACT

An ameliorant of cerebral circulation which contains 2-carbamoyloxymethyl-4-(2,3-dichlorophenyl)-6-methyl-1,4-dihydropyridine-3,5-dicarboxylic acid 3-isopropyl ester 5-methyl ester as an active ingredient.

2 Claims, No Drawings

METHOD OF AMELIORATING CEREBRAL CIRCULATION

This is a Division of application Ser. No. 08/282,657 filed on Jul. 29, 1994, now U.S. Pat. No. 5,444,077, which is a Continuation of application Ser. No. 07/645,309, filed on Jan. 24, 1991, now abandoned, which is a Continuation of application Ser. No. 07/254,106, filed on Oct. 6, 1988, now abandoned.

The present invention is an invention useful in the pharmaceutical field. More particularly, it relates to an ameliorant of cerebral circulation containing 2-carbamoyloxymethyl-4-(2,3-dichlorophenyl)-6-methyl-1,4-dihydropyridine-3,5-dicarboxylic acid 3-isopropyl ester 5-methyl ester as an active ingredient, and a levo-rotatory optical isomer of 2-carbamoyloxymethyl-4-(2,3-dichlorophenyl)-6-methyl-1,4-dihydropyridine-3,5-dicarboxylic acid 3-isopropyl ester 5-methyl ester as a novel compound, processes for its production and its use.

2-Carbamoyloxymethyl-4-(2,3-dichlorophenyl)-6-methyl-1,4-dihydropyridine-3,5-dicarboxylic acid 3-isopropyl ester 5-methyl ester is a compound which was synthesized for the first time by the researchers of the applicant company. It has vasodilation activities and hypotensive activities, and thus is expected to be useful as a drug for the treatment of various heart diseases such as cardiac insufficiency, angina pectoris or myocardial infarction, or as a hypotensive drug (Japanese Journal of Pharmacology, Vol. 40, p.399–409 (1986) and Japanese Unexamined Patent Publication No. 152373/1984).

2-Carbamoyloxymethyl-4-(2,3-dichlorophenyl)-6-methyl-1,4-dihydropyridine-3,5-dicarboxylic acid 3-isopropyl ester 5-methyl ester (hereinafter referred to simply as NB-818) has the following formula:

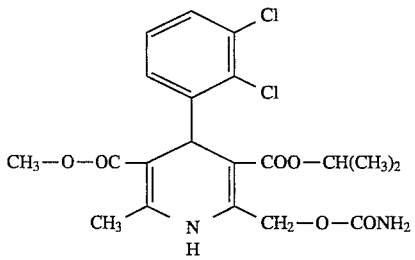

On the other hand, some of 1,4-dihydropyridine derivatives are known to be useful as ameliorants of cerebral circulation (Calcium Entry Blockers and Tissue Protection, compiled by T. Godfraind, published by Raven Press (1987) and Japanese Unexamined Patent Publication No. 109384/1975 and Japanese Examined Patent Publication No. 135776/1979).

However, such conventional compounds are inadequate in the selectivity for an organ and the strength and effective period of the activities, and a superior ameliorant of cerebral circulation has been desired.

NB-818 has one asymmetric carbon atom and from the viewpoint of the stereochemistry, it is expected to have optical isomers due to the asymmetric carbon atom. However, in this respect, nothing is disclosed or suggested in the above-mentioned publications or literatures.

It is an object of the present invention to overcome the drawbacks of the conventional ameliorants of cerebral circulation such as insufficiency in the activities or in the selectivity for an organ and inadequacy of the effective period and to provide a specific ameliorant of cerebral circulation having little side-effects.

Another object of the present invention is to provide a compound having excellent pharmacological activities and a high level of safety as a desired property as a drug.

The present inventors have conducted extensive researches on 1,4-dihydropyridine derivatives having a carbamoyloxymethyl group at the 2-position of the pyridine ring. As a result of detailed studies of the pharmacological activities of these compounds, it has now been found that NB-818 is particularly superior in the selectivity for the brain and has a distinctly superior ameliorating effect for cerebral circulation as compared with conventional compounds of this type. Further, the present inventors have for the first time separated the levo-rotatory optical isomer and the dextro-rotatory optical isomer of NB-818 and have found that the levo-rotatory optical isomer of NB-818 has a very excellent characteristic pharmacological effects as compared with the dextro-rotatory optical isomer of NB-818. The present invention has been accomplished on the basis of these discoveries.

The present invention provides an ameliorant of cerebral circulation which contains NB-818 i.e. 2-carbamoyloxymethyl-4-(2,3-dichlorophenyl)-6-methyl-1,4-dihydropyridine-3,5-dicarboxylic acid 3-isopropyl ester 5-methyl ester as an active ingredient.

The present invention also provides the levo-rotatory isomer of NB-818, processes of its production and its use.

Firstly, the ameliorant of cerebral circulation containing NB-818 will be described.

NB-818 used in the present invention is a known compound, which can be prepared, for example, by a process disclosed in e.g. Japanese Unexamined Patent Publication No. 152373/1984.

The ameliorant of cerebral circulation of the present invention may be composed solely of NB-818 or a combination of NB-818 with a pharmaceutically acceptable additive.

The pharmaceutically acceptable additive may be an additive which is commonly used in the field of the drug formulation, such as gelatin, lactose, sucrose, titanium oxide, starch, crystalline cellulose, hydroxypropylmethyl cellulose, carboxymethyl cellulose, corn starch, microcrystalline wax, white vaseline, magnesium metasilicate aluminate, anhydrous calcium phosphate, citric acid, trisodium citrate, hydroxypropyl cellulose, sorbitol, sorbitan fatty acid ester, polyvinylpyrrolidone, magnesium stearate, light anhydrous silicic acid, talc, vegetable oil, benzyl alcohol, gum arabic, propylene glycol or polyalkylene glycol.

The mixture with such an additive may be formulated into various formulations including solid formulations such as tablets, capsules, granules, powders or suppositories and liquid formulations such as syrups, elixirs or injection solutions. Such formulations can be prepared by conventional methods commonly used in the drug formulation. The liquid formulations may be in such a form that they can be dissolved or suspended in water or other suitable medium at the time of their use. Particularly in the case of an injection drug, it may be dissolved in an isotonic sodium chloride solution or a glucose solution as the case requires, and a buffer agent or a storage stabilizer may further be added. Further, the present invention includes various formulations to which drug formulation techniques are applied to improve the values of NB-818 as medicines. Specific examples of such formulations include solid solution (solid dispersion) drugs having excellent immediate effect or readily absorbable properties and gradual releasing drugs to prolong the effective period or to reduce the side effects.

Such formulations contain NB-818 usually in an amount of from 1.0 to 100% by weight, preferably from 1.0 to 60% by weight, based on the entire formulations. Further, such formulations may contain other compounds which are effective for treatment.

When NB-818 of the present invention is used as an ameliorant of cerebral circulation, the administration may be oral or non-oral such as intravenous or subcutaneous injection. The dose and the number of times of administration vary depending upon the difference of patients, the degree of the disease or the age and body weight of the patient, or when combined with other drugs, the types of such drugs. However, in the case of oral administration, a daily dose of from 0.01 to 1 mg/kg per adult is administered from once to a few times a day. In the case of non-oral administration, a daily dose of from 0.01 to 0.2 mg/kg per adult is administered from once to a few times a day.

The pharmacological activities of the ameliorant of cerebral circulation of the present invention are effective quite selectively to the cerebral circulation system, and the effectiveness lasts for a long period of time. As compared with compounds having chemical structures similar to the structure of NB-818 as the ameliorant of cerebral circulation of the present invention, i.e. as compared with compounds A, B, C and D as described hereinafter and with nimodipine and nicardipine, NB-818 as the ameliorant of cerebral circulation of the present invention is superior in each of the intensity of the activities, the effective period of the activities and the selectivity for cerebral vessels. Further, the ameliorant of cerebral circulation of the present invention has in addition to an ordinary effect to ameliorate the cerebral circulation an effect to activate the cerebral metabolism and an effect to protect the brain. Accordingly, it is useful in a wide range for the treatment or prevention of a series of diseases generally called cerebral insufficiency or disturbance of cerebral circulation, including, for example, cerebral arteriosclerosis, cerebral apoplexy, cerebral infarction, cerebral ischemia, traumatic cerebral damage, decrease of cerebral functions, defects of memory, dementia and headache.

The toxicity ($LD_{50}$) of the ameliorant of cerebral circulation of the present invention is extremely low ($LD_{50}$ upon oral administration of NB-818 to rats is at least 3 g/kg). Thus, it is particularly advantageous for the treatment and prevention of the above diseases, for which continuous administration for a long period of time is obliged. Thus, its value as a pharmaceutical is very high.

Now, the pharmacological test examples of the compound of the present invention will be given, from which the usefulness of the compound will be evident.

PHARMACOLOGICAL TEST EXAMPLE 1

Effect to increase the blood flow of the vertebral artery

A male or female beagle dog having a body weight of about 10 kg was anesthetized by subcutaneous administration of 35 mg/kg of sodium pentobarbital, and the level of anesthesia was maintained by continuous injection of from 4 to 6 mg/kg/hr of sodium pentobarbital.

The test was conducted by maintaining the blood gases under optimum conditions under artificial respiration. A drug was dissolved in a 0.9 wt % saline containing 10% by weight of polyethylene glycol and 10% by weight of ethanol, and a predetermined amount of the solution was intravenously or intraduodenally injected to the beagle dog. Then, the blood flow, the blood pressure and the heart rate were measured.

The blood flow was measured by an electromagnetic flow meter by means of blood flow probes attached to the vertebral artery and the femoral artery of the beagle dog. The blood pressure was measured by a pressure transducer connected to a canule inserted to the left femoral artery of the beagle dog. The results are shown in Tables 1 and 2.

DRUGS

Compound A
2-Carbamoyloxymethyl-4-(2,3-dichlorophenyl)-6-methyl-1,4-dihydropyridine-3,5-dicarboxylic acid 3,5 -dimethyl ester Compound B
2-Carbamoyloxymethyl-4-(2,3-dichlorophenyl)-6-methyl-1,4-dihydropyridine-3,5-dicarboxylic acid 3-ethyl ester 5-methyl ester Compound C
2-Carbamoyloxymethyl-4-(2,3-dichlorophenyl)-6-methyl-1,4-dihydropyridine-3,5-dicarboxylic acid 3-propyl ester 5-methyl ester Compound D
2-Carbamoyloxymethyl-4-(2,3-dichlorophenyl)-6-methyl-1,4-dihydropyridine-3,5-dicarboxylic acid 3-butyl ester 5-methyl ester (The above compounds A, B, C and D are all disclosed in Japanese Unexamined Patent Publication No. 152373/1984.)

TABLE 1

| Drug | | Dose (mg/kg) | Administration route | Number of animals | Change (%) | | | Effective period (Half-life period) min |
|---|---|---|---|---|---|---|---|---|
| | | | | | Vertebral artery blood flow | Femoral artery blood flow | Blood pressure | |
| NB-818 | | 0.01 | iv | 8 | +109 | +12 | −14 | 57 |
| Comparative | Compound A | 0.01 | iv | 3 | +76 | +14 | −13 | 9 |
| | Compound B | 0.01 | iv | 3 | +50 | +16 | −14 | 36 |
| | Compound C | 0.01 | iv | 3 | +95 | +20 | −15 | 42 |
| | Compound D | 0.01 | iv | 3 | +80 | +13 | −14 | 44 |

Note: iv: intravenous administration

TABLE 2

| Drug | Dose (mg/kg) | Administration route | Number of animals | Change (%) Vertebral artery blood flow | Femoral artery blood flow | Blood pressure | Effective period (Half-life period) (min) |
|---|---|---|---|---|---|---|---|
| NB-818 | 0.1 | id | 4 | +135 | +36 | −18 | >300 |
| Nimodipine | 0.3 | id | 4 | +102 | +75 | −29 | 150 |

Note: id: intraduodenal administration

As shown in Tables 1 and 2, NB-818 selectively increased the vertebral artery blood flow as an index of the cerebral blood flow at a dose level where the influence over the blood pressure and the heart rate is minimum. Further, it is significantly superior to the comparative drugs in the blood flow increasing rate and in the effective period of the increase.

PHARMACOLOGICAL TEST EXAMPLE 2

Effect to increase the cerebral regional blood flow in rabbits

A male rabbit having a body weight of about 3 kg was immobilized by intravenous injection of gallamine (2–3 mg/kg) and secured to an apparatus for fixing the brain position. Then, platinum electrodes for measuring hydrogen gas clearance were inserted to the top of cerebral cortex, to the center of the cerebellum and to the femoral muscle, and the blood flows were measured. The drug was dissolved in a 0.9 wt % saline containing 10% by weight of polyethylene glycol and 10% by weight of ethanol, and the solution was intravenously injected.

The results are shown in Table 3.

PHARMACOLOGICAL TEST EXAMPLE 3

Effect to increase the cerebral regional blood flow in monkeys

A male Rhesus monkey having a body weight of from 5.0 to 11.0 kg was anesthetized with ketamine hydrochloride (1 mg/kg by intravenous injection) and sodium pentobarbital (30 mg/kg by intraperitoneal injection), and an endotracheal tube was inserted for artificial respiration. Then, the animal's head was fixed to a stereotaxic apparatus. The cerebral blood flow was calculated from the hydrogen gas clearance curve measured by means of needle type electrodes for hydrogen gas clearance inserted to the cerebral cortex after incising the head and boring a hole in the occipital lobe.

The drug was dissolved in a 0.9 wt % saline containing 10% by weight of polyethylene glycol 300 and 10% by weight of ethanol, and the solution was intravenously administered. The results are shown in Table 4.

TABLE 3

| Drug | Dose (mg/kg) | Number of animals | Blood flow change (%) Cerebral blood flow | Cerebellum blood flow | Femoral muscle blood flow | Effective period (Half-life period) (min) |
|---|---|---|---|---|---|---|
| NB-818 | 0.01 | 6 | +82 | +85 | +3 | 44.6 |
| Nimodipine | 0.01 | 6 | +68 | +55 | −5 | 20.6 |
| Nicardipine | 0.01 | 6 | +56 | +57 | +22 | 31.6 |

As is evident from Table 3, NB-818 increased the blood flows governed, respectively, by the vertebral artery system (the artery system governing the cerebral cortex blood flow) and by the internal carotid artery system (the artery system governing the cerebellum blood flow), which govern the cerebral blood flow. The effect and the effective period thereof were superior to those of commercially available ameliorants of cerebral circulation such as nicardipine and nimodipine.

TABLE 4

| Drug | Dose (mg/kg) | Number of animals | Change (%) Cerebral cortex blood flow | Blood pressure | Heart rate | Effective period (Half-life period) (min) |
|---|---|---|---|---|---|---|
| NS-818 | 0.01 | 5 | +28 | −20 | +16 | >60 |
| Nicardipine | 0.01 | 5 | +16 | −24 | +18 | <30 |

As is evident from Table 4, NB-818 remarkably increased the cerebral blood flow of monkeys. It was superior to nicardipine in the effect and the effective period.

PHARMACOLOGICAL TEST EXAMPLE 4

Effect to prolong the life in the cerebral isochemia models of Mongolian gerbils A male Mongolian gerbil having a body weight of about 70 g was anesthetized by intraperitoneal administration of 70 mg/kg of ketamine hydrochloride. Then, left and right common carotid arteries were exposed and closed by scorbil clips for 20 minutes. Then, the clips were removed to regain the blood flow. Thirty minutes later, a drug dissolved in a 0.9 wt % saline containing 10% by weight of polyethylene glycol 300 and 10% by weight of ethanol, was intraperitoneally administered. The effect to prolong the life was determined by observing mortality and the neurotic symptom during 8 hours or 24 hours from the administration of the drug.

The results are shown in Table 5.

TABLE 5

| Drug | Dose (mg/kg) | Number of animals | Mortality (%) 0-8 hours | 0-24 hours |
|---|---|---|---|---|
| Control | — | 19 | 100 | 100 |
| NB-818 | 0.01 | 13 | 38.5 | 76.9 |
| Nimodipine | 0.01 | 12 | 83.3 | 91.7 |
| Nicardipine | 0.01 | 12 | 83.3 | 91.7 |

As is evident from Table 5, NB-818 exhibits a distinct effect to prolong the life at such a low dosage at which no adequate effects are obtainable by the comparative drugs such as nimodipine and nicardipine.

PHARMACOLOGICAL TEST EXAMPLE 5

Effect against experimentally induced amnesia

By using male rats having a body weight of about 200 g, the antiamnesic effect was examined on the basis of one trial passive avoidance reaction as an index. Namely, a rat is put in a light chamber of an operant box comprising the light chamber and a dark chamber, and when the rat entered into the dark chamber, an electric stimulation (5 mA for 10 seconds) was applied from the floor and immediately an electric shock (30 mA, 0.75 second) (hereinafter referred to simply as ECS) was applied to the head of the rat. Two hours or 24 hours after the ECS, the rat was put in the light chamber, and the time until the rat entered from the light chamber to the dark chamber (the latent reaction time) was measured.

The drug was suspended in a 0.5 wt % methyl cellulose and orally administered three times at intervals of 24 hours so that the final administration was conducted one hour prior to ECS.

The results are shown in Table 6.

In a separate test, the drug was orally administered at the same time as ECS, and the latent reaction time was measured two hours later, or NB-818 was again administered 22 hours later and then the latent reaction time was measured two hours later.

The results are shown in Table 7.

TABLE 6

Effect against amnesia induced by ECS
(Pretreatment with drug administration)

| Drug | Dose (mg/kg, p.o.) | Number of animals | Latent reaction time (seconds) Acquisition test | 2 hours later | 24 hours later |
|---|---|---|---|---|---|
| Control | — | 20 | 8.6 ± 1.3 | 49.2 ± 8.1 | 85.6 ± 22.0 |
| NB-818 | 3 | 19 | 11.4 ± 1.3 | 128.8 ± 21.8* | 189.6 ± 24.6* |
| Nimodipine | 3 | 19 | 9.6 ± 1.3 | 103.9 ± 22.2* | 132.1 ± 25.5* |

*Significant difference from the control group $P < 0.05$

TABLE 7

Effect against amnesia induced by ECS
(Post-treatment with drug administration)

| Drug | Dose (mg/kg, p.o.) | Number of animals | Latent reaction time (seconds) Acquisition test | 2 hours later | 24 hours later |
|---|---|---|---|---|---|
| Control | — | 32 | 9.0 ± 1.5 | 30.6 ± 3.0 | 42.5 ± 9.0 |
| NB-818 | 1 | 20 | 8.3 ± 1.2 | 88.5 ± 17.9* | 111.8 ± 21.5* |

*Significant difference from the control group $P < 0.05$

As is evident from Tables 6 and 7, NB-818 significantly extended the latent reaction time over the non-administered group of control in both cases. Further, it was superior to nimodipine in the prolongation of the latent reaction time.

Now, the levo-rotatory optical isomer of NB-818, the processes for its preparation and the use thereof will be described.

Firstly, the processes for the levo-rotatory optical isomer of NB-818 will be described. The optical isomer can be prepared by the following process A or B.

Process A

The levo-rotatory optical isomer (1) of 2-carbamoyloxymethyl-4-(2,3-dichlorophenyl)-6-methyl-1,4-dihydropyridine-3,5-dicarboxylic acid 3-isopropyl ester 5-methyl ester of the present invention can be prepared by (a) reacting 2,3-dichlorobenzaldehyde of the formula:

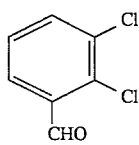

(S)-(+)-β-methoxyphenethyl acetoacetate of the formula:

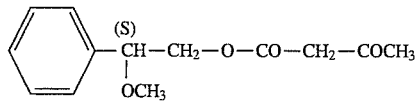

and isopropyl 4-acetoxy-3-aminocrotonate of the formula:

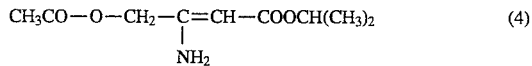

or (b) reacting 2,3-dichlorobenzaldehyde (2), isopropyl 4-acetoxyacetoacetate of the formula:

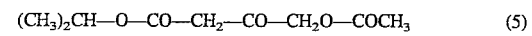

and (S)-(+)-β-methoxyphenethyl 3-aminocrotonate of the formula:

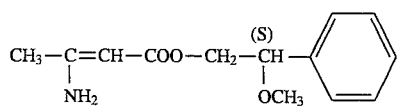

or (c) reacting (S)-(+)-β-methoxyphenethyl 2,3-dichlorobenzylidene)acetoacetate of the formula:

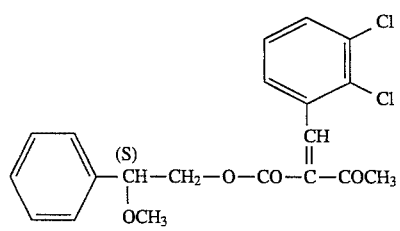

with isopropyl 4-acetoxy-3-aminocrotonate of the formula:

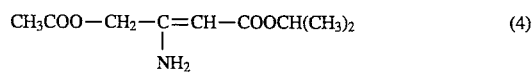

or (d) reacting isopropyl 4-acetoxy-2-(2,3-dichlorobenzylidene)acetoacetate of the formula:

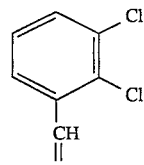

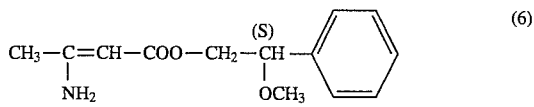

with (S)-(+)-β-methoxyphenethyl 3-aminocrotonate of the

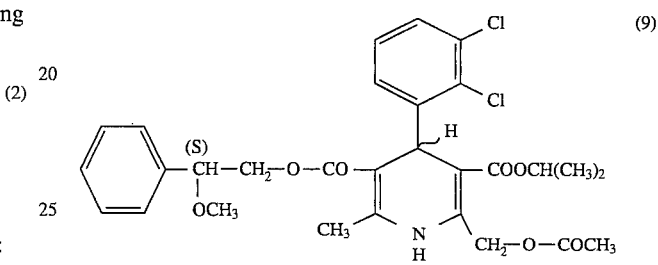

to obtain 2-acetoxymethyl-4-(2,3-dichlorophenyl)-6-methyl-1,4-dihydropyridine-3,5-dicarboxylic acid 3-isopropyl ester 5-(S)-(+)-β-methoxyphenethyl ester of the formula:

then, separating and purifying the 1,4-dihydropyridine to obtain an appropriate optical isomer (10) of 2-acetoxymethyl-4-(2,3-dichlorophenyl)-6-methyl-1,4-dihydropyridine-3,5-dicarboxylic acid 3-isopropyl ester 5-(S)-(+)-β-methoxyphenethyl ester, then treating the appropriate optical isomer (10) with a base to obtain an appropriate optical isomer (11) of 2-hydroxymethyl-4-(2,3-dichlorophenyl)-6-methyl-1,4-dihydropyridine-3,5-dicarboxylic acid 3-isopropyl ester 5-(S)-(+)-β-methoxyphenethyl ester, then protecting a hydroxyl group in the hydroxymethyl product (11), treating it with sodium methoxide in methanol, then treating it with an acid to obtain an appropriate optical isomer (12) of 2-hydroxymethyl-4-(2,3-dichlorophenyl)-6-methyl-1,4-dihydropyridine-3,5-dicarboxylic acid 3-isopropyl ester 5-methyl ester, and reacting the diester compound (12) with chlorosulfonyl isocyanate.

Each of the reactions (a), (b), (c) and (d) proceeds even in the absence of a solvent. However, it is advantageous to conduct such a reaction in a solvent which does not adversely affect the reaction, for example, an alcohol such as methanol, ethanol, propanol, isopropanol or butanol, dioxane, dimethylformamide, dimethylsulfoxide, acetonitrile, acetone, ethyl acetate, benzene, chloroform, water or a solvent mixture thereof. The respective reactions can be conducted by using substantially the same molar amounts of the reactants and mixing and heating them. As a catalyst to facilitate the reactions, an acid such as acetic acid, a base such as piperidine or a salt thereof may be added.

The compound (4) and the compound (6) can be prepared by reacting the compound (3) or the compound (5) with acetic acid or ammonium acetate in benzene, followed by azeotropic removal of water. The compound (4) or the compound (6) thus obtained may be isolated before use, or may be used as the starting material without being isolated.

The step of the optical resolution of the compound (9) obtained by the above-mentioned step, to produce its appropriate optical isomer (10) can be conducted by a method per se known such as a fractional crystallization method or a separation purification method by means of column chromatography or high performance liquid chromatography.

Here, a separation purification method by means of high performance liquid chromatography will be described as an example. Namely, it is possible to separate from the compound (9) its appropriate optical isomer (10) by conducting high performance liquid chromatography at a flow rate of 20 ml/min by using a column of e.g. Senshu Pak Solica 5301-N® (manufactured by Senshu Kagaku Co.) and a solvent mixture of hexane/ethyl acetate as a mobile phase and using an ultraviolet detector (λ254 nm).

The step of treating the appropriate optical isomer (10) with a base to convert it to the compound (11), can be conducted by treating it with a base such as sodium methoxide at room temperature for from 10 minutes to one hour in a solvent which does not adversely affect the reaction, such as methanol.

The step of protecting the hydroxyl group of the compound (11) obtained in the above step, with a usual protecting reagent, followed by ester interchange with sodium methoxide and then by the removal of the protecting group with an acid to obtain the compound (12), can be conducted by reacting it with isopropenyl methyl ether at room temperature for from 30 minutes to 2 hours in a solvent such as methylene chloride in the presence of a base such as pyridine and an acid such as p-toluene sulfonic acid, to protect the hydroxyl group in the compound (11), followed by treatment with sodium methoxide for from 20 to 40 hours under heating and refluxing in methanol. Then, after cooling, the reaction mixture is treated with an acid such as acetic acid at room temperature for from 5 to 30 hours, to remove the protecting group.

The step of reacting chlorosulfonyl isocyanate to the compound (12) to obtain the compound (1) as the desired compound of the present invention, can be conducted by reacting chlorosulfonyl isocyanate at room temperature for from 20 to 30 minutes in a solvent which does not adversely affect the reaction, such as benzene, and then an excess of chlorosulfonate is decomposed by an addition of water.

The product obtained in each of the above steps, may be purified by e.g. column chromatography, a solvent extraction method, a precipitation method or a recrystallization method, if necessary. In some cases, the product may be used for the subsequent step without purification.

Process B

The levo-rotatory optical isomer (1) of 2-carbamoyloxymethyl-4-(2,3-dichlorophenyl)-6-methyl-1,4-dihydropyridine-3,5-dicarboxylic acid 3-isopropyl ester 5-methyl ester of the present invention can be prepared by (e) reacting 2,3-dichlorobenzaldehyde of the formula:

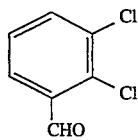

(2)

isopropyl 4-carbamoyloxyacetoacetate of the formula:

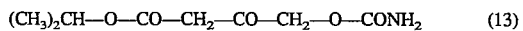

(13)

and methyl 3-aminocrotonate of the formula:

(14)

or (f) reacting 2,3-dichlorobenzaldehyde (2), methyl acetoacetate of the formula:

(15)

and isopropyl 3-amino-4-carbamoyloxycrotonate of the formula:

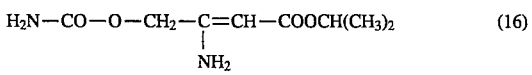

(16)

or (g) reacting isopropyl 4-carbamoyloxy-2-(2,3-dichlorobenzylidene)acetoacetate of the formula:

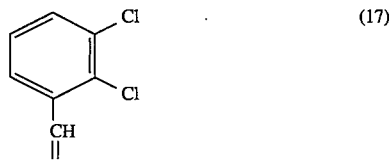

(17)

with methyl 3-aminocrotonate of the formula:

(14)

or (h) reacting methyl 2-(2,3-dichlorobenzylidene)acetoacetate of the formula:

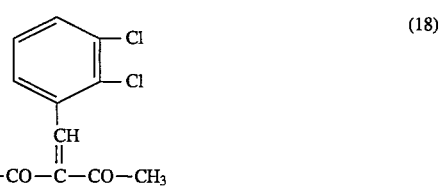

(18)

with isopropyl 3-amino-4-carbamoyloxycrotonate of the formula:

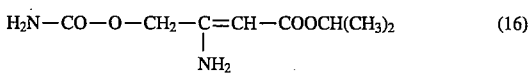

(16)

or (i) reacting methyl 2-(2,3-dichlorobenzylidene)acetoacetate of the formula:

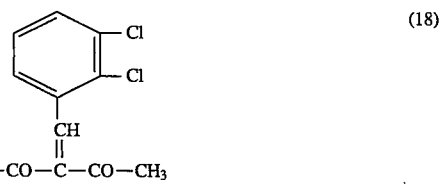

(18)

isopropyl 4-carbamoyloxy tetrolate of the formula:

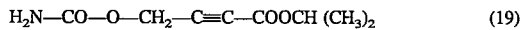

(19)

and ammonia or its salt, or (j) reacting isopropyl 4-carbamoyloxy-2-(2,3-dichlorobenzylidene)acetoacetate of the formula:

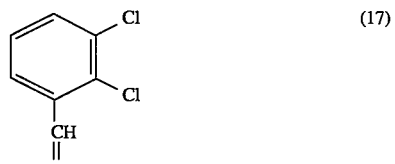

(17)

methyl tetrolate of the formula:

(20)

and ammonia or its salt, or (k) reacting 2,3-dichlorobenzaldehyde (2), isopropyl 4-carbamoyloxy tetrolate of the formula:

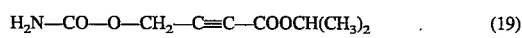

(19)

methyl acetoacetate of the formula:

$$CH_3\text{---}CO\text{---}CH_2\text{---}COOCH_3 \quad (15)$$

and ammonia or its salt, or (1) reacting 2,3-dichlorobenzaldehyde (2), methyl tetrolate of the formula:

$$CH_3\text{---}C\equiv C\text{---}COOCH_3 \quad (20)$$

isopropyl 4-carbamoyloxy acetoacetate of the formula:

$$(CH_3)_2CH\text{---}O\text{---}CO\text{---}CH_2\text{---}CO\text{---}CH_2\text{---}O\text{---}CONH_2 \quad (13)$$

and ammonia or its salt, to obtain 2-carbamoyloxymethyl-4-(2,3-dichlorophenyl)-6-methyl-1,4-dihydropyridine-3,5-dicarboxylic acid 3-isopropyl ester 5-methyl ester of the formula:

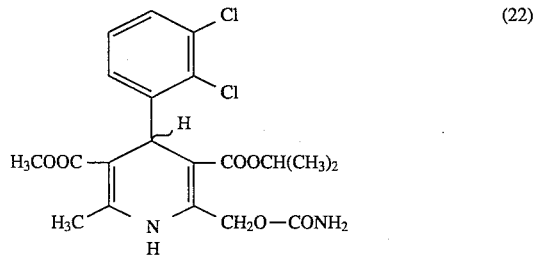

and then subjecting the 1,4-dihydropyridine derivative (22) to optical resolution.

The reactions of the steps (e), (f), (g), (h), (i), (j), (k) and (1) can be conducted, for example, by the methods disclosed in Japanese Unexamined Patent Publication No. 152373/1984 or by similar methods. Namely, the reactions of these steps may proceed in the absence of a solvent. However, it is advantageous to conduct such reactions in a solvent which does not adversely affect the reaction, for example, in an alcohol such as methanol, ethanol, propanol, isopropanol or butanol, dioxane, dimethylformamide, dimethylsulfoxide, acetonitrile, acetone, ethyl acetate, benzene, chloroform, water or a solvent mixture thereof. The reactions can be conducted by using substantially equal molar amounts of the respective reactants and mixing and heating them. As a catalyst to facilitate the reaction, an acid such as acetic acid, a base such as piperidine or a salt thereof may be added.

Further, compound (16) can be prepared by the process disclosed in Japanese Unexamined Patent Publication No. 67257/1984. Likewise, the compound (19) can be produced by a process disclosed in 42355/1984 or by a similar method.

As the ammonia salt to be used in the steps (i), (j), (k) and (1), an ammonium salt of an organic acid such as acetic acid, formic acid, tartaric acid or benzoic acid, or an ammonium salt of an inorganic acid such as carbonic acid or boric acid may be used.

The step of the optical resolution of the compound (22) obtained by the above process, to obtain the compound (1) as the desired compound of the present invention, can be conducted by a method per se known, such as by fractional crystallization or a separation purification method such as column chromatography by means of silica gel or high speed liquid chromatography. Here, the separation purification by means of high speed liquid chromatography will be described as an example. Namely, it is possible to obtain from the compound (22) its levo-rotatory optical isomer by conducting high performance liquid chromatography at a flow rate of 20 ml/min by using a cellulose derivative type packing agent such as Chiralcel® (manufactured by Daicel Chemical Industries) and a solvent mixture of hexane/isopropanol as a mobile phase and using an ultraviolet detector (λ254 nm).

Now, the pharmacological test examples of the desired compound of the present invention will be described to specifically show the usefulness.

PHARMACOLOGICAL TEST EXAMPLE 6

Effect to increase the blood flow of the vertebral artery

A male or female beagle dog having a body weight of about 10 kg was anesthetized by subcutaneous administration of 35 mg/kg of sodium pentobarbital, and the level of anesthesia was maintained by continuous injection of from 4 to 6 mg/kg/hr of sodium pentobarbital.

The test was conducted by maintaining the blood gases under optimum conditions under artificial respiration. A drug was dissolved in a 0.9 wt % saline containing 10% by weight of polyethylene glycol and 10% by weight of ethanol, and a predetermined amount of the solution was intravenously injected to the beagle dog. Then, the blood flow, the blood pressure and the heart rate were measured.

The blood flow was measured by an electromagnetic flow meter by means of blood flow probes attached to the vertebral artery and the femoral artery of the beagle dog. The blood pressure was measured by a pressure transducer connected to a canule inserted to the left femoral artery of the beagle dog. Further, the heart rate was measured by a heart rate counter based on the pulse wave of blood pressure. The results are shown in Table 8.

The levo-rotatory optical isomer of 2-carbamoyloxymethyl-4-(2,3-dichlorophenyl)-6-methyl-1,4-dihydropyridine-3,5-dicarboxylic acid 3-isopropyl ester 5-methyl ester will be hereinafter referred to simply as (−)-NB-818, and the dextro-rotatory optical isomer thereof will be referred to simply as (+)-NB-818.

TABLE 8

| Drug | Dose (mg/kg) | Number of animals | Change (%) | | | | Effective period (Half-life period) (min) |
| | | | Vertebral artery blood flow | Femoral artery blood flow | Blood pressure | Heart rate | |
| --- | --- | --- | --- | --- | --- | --- | --- |
| (−)-NB-818 | 0.01 | 5 | +123.2 | +3.3 | −26.6 | +3.4 | 44 |
| (+)-NB-818 | 0.1 | 5 | +56.8 | +18.8 | −8.1 | +3.8 | 15.5 |
| Nimodipine | 0.3* | 4 | +102 | +75 | −29 | −23 | 150 |

*intraduodenal administration

As is evident from Table 8, (−)-NB-818 of the present invention is superior to (+)-NB-818 in both the effect to increase the vertebral artery blood flow and the intensity and effective period of the effect. Further, (−)-NB-818 of the present invention selectively increase the vertebral blood flow governing the cerebral circulation and thus has very excellent activities as a curing agent for cerebral diseases.

PHARMACOLOGICAL TEST EXAMPLE 7

Vasodilatory effect on the isolated vascular smooth muscle

A male white house rabbit having a body weight of about 2.5 kg was anesthetized with pentobarbital, and sacrificed by bleeding from the femoral artery. Immediately, the superior mesenteric artery was excised. The fatty tissue, the connective tissue, etc. around the blood vessel were removed with a Krebs solution (composition: NaCl 115.0 mmol, KCl 4.7 mmol, $CaCl_2$ 2.5 mmol, $MgCl_2.6H_2O$ 1.2 mmol, $KH_2PO_4$ 1.2 mmol, $NaHCO_3$ 25.0 mmol, glucose 5.56 mmol) under observation by a microscope, to obtain a spiral strip having a width of 1 mm and a length of 15 mm.

In accordance with a usual method, the Krebs solution was filled in a magnus tube having a capacity of 20 ml and kept at a temperature of 37° C., and a gas mixture of 95% $O_2$ and 5% $CO_2$ was supplied. A resting tension of 1 g was exerted to each strip. The reaction of the strip was isometrically recorded. The Krebs solution was changed every about 20 minutes, and the strip was left for one hour. After the strip was stabilized, trial contraction was conducted twice by an addition of 50 mmol KCl, and the test was started. Then, 50 mmol KCl was administered, and when the contraction reached a constant level, the drug was added cumulatively increasing manner starting at a low dose to induce the vasodilation. $10^{-4}M$ Papaverine was added at the end of each series of experiments, and the relaxation induced by paraverine was taken as 100%. The concentration of each drug which inhibited the contractill response by 50% ($ED_{50}$ value) was estimated from the dose-response curve thereby obtained.

The results are shown in Table 9.

A dimethylsulfoxide solution having a drug concentration of $10^{-2}M$ was diluted with a 50% dimethylsulfoxide aqueous solution to prepare sample solutions having concentrations of $10^{-3}M$ and $10^{-4}M$, respectively. A sample solution having a concentration of not higher than $10^{-5}M$ was prepared by dilution with a 20% dimethylsulfoxide aqueous solution. The concentration of dimethylsulfoxide in the magnus tube was not higher than 0.1%.

TABLE 9

| Drug | $ED_{50}$ (M) | n |
| --- | --- | --- |
| (−)-NB-818 | (1.2 ± 0.2*) × $10^{-10}$ | 4 |
| (+)-NB-818 | (4.1 ± 1.3*) × $10^{-7}$ | 3 |

*Mean ± SE

As is evident from Table 9, (−)-NB-818 is superior to (+)-NB-818 in the vasodilatory effect on the isolated blood vessel of a rabbit.

PHARMACOLOGICAL TEST EXAMPLE 8

Bonding effect to a dihydropyridine type calcium channel receptor

The brain homogenate of a SD type rat was subjected to ultracentrifugal separation to obtain a cerebral membral fraction of 48,000 G, and the fraction was suspended in a tris hydrochloric acid buffer solution (pH 7.4) to obtain a membrane fraction receptor.

To a tris hydrochloric acid buffer solution (pH 7.4), 200 µl (containing 4 mg of tissue by wet weight) of the suspension of the membrane fraction receptor, a drug tris hydrochloric acid buffer solution and a (+)-[$^3$H] isladipine phosphate buffer solution were added to bring the total amount to 3 ml, and the mixture was maintained at 25° C. for 3 hours. Then, 3 ml of a tris hydrochloric acid buffer solution cooled with ice was added thereto to stop the reaction, and the mixture was immediately subjected to filtration with a Whatman GF/C glass fiber filter, followed by washing three times with 3 ml of a tris hydrochloric acid buffer solution cooled with ice. Then, the radioactivity on the filter was measured by a liquid scintillation counter.

The non-specific bonding amount was measured by an addition of 1 µM of (±)-isladipine, and it was subtracted from the total bonding amount measured without such an addition, to obtain the specific bonding amount. From the specific bonding amounts at various drug concentrations, a inhibitory concentration ($IC_{50}$) against the bonding of (±)-[$^3$H] isladipine was calculated. The results are shown in Table 10.

TABLE 10

| Drug | $ED_{50}$ (M) | n |
| --- | --- | --- |
| (−)-NB-818 | (3.7 ± 0.8*) × $10^{-10}$ | 4 |
| (+)-NB-818 | (8.0 ± 3.2*) × $10^{-7}$ | 3 |

*Mean ± SE

As is evident from Table 10, (−)-NB-818 is superior to (+)-NB-818 in the affinity to the calcium channel receptor.

From the results of the foregoing Pharmacological Test Examples, it is evident that (−)-NB-818 of the present invention has excellent vasodilation activities, and such activities are specific to cerebral blood vessels. Thus, it has extremely useful properties as a vasodilator, particularly as an ameliorant of cerebral circulation.

When (−)-NB-818 of the present invention is used as a hypotensive drug or an ameliorant of cerebral circulation, (−)-NB-818 may be used alone or in combination with a pharmaceutically acceptable additive in a drug formulation. The drug formulations containing (−)-NB-818, the methods for such drug formulations and the manners for their administration may be the same as described above with respect to NB-818.

When (−)-NB-818 is used as a hypotensive drug or an ameliorant of cerebral circulation, the dose may be the same as described with respect to NB-818. However, the dose may be increased or reduced in accordance with the doctor's prescription.

Now, the present invention will be described in further detail with reference to Examples. However, it should be understood that the present invention is by no means restricted to such specific Examples.

EXAMPLE 1

960 g of lactose (100 mesh, manufactured by DMV Co.) was put into a centrifugal flow type coating machine (CF-360, manufactured by Freund Sangyo K.K.). Then, 1,000 ml of an ethanol/methylene chloride solution (1/1, v/v) having 10 g of NB-818 and 30 g of hydroxypropylmethyl cellulose 2910 (HMPC 2910, manufactured by Shin-etsu Chemical Co., Ltd.) completely dissolved, was spray-coated thereto by a usual method to obtain granules. The granules were dried at 40° C. for 4 hours and then the granule size was adjusted by a usual method to obtain a granule drug.

EXAMPLE 2

1,590 g of lactose (100 mesh, manufactured by DMV Co.) was introduced into a centrifugal flow type coating machine (CF-360, manufactured by Freund Sangyo K.K.). Then, 5,000 ml of an ethanol/methylene chloride solution (1/1, v/v) having 100 g of NB-818 and 300 g of hydroxypropylmethyl cellulose 2910 (HMPC 2910, manufactured by Shin-etsu Chemical Co., Ltd.) completely dissolved, was spray-coated thereto to obtain granules. The granules were dried at 40° C. for 4 hours, and then the granule size was adjusted by a usual method. Then, 10 g of magnesium stearate was added thereto, and the mixture was packed in capsules to obtain a capsule drug.

EXAMPLE 3

50 g of NB-818, 245 g of lactose (Dilactose: manufactured by Freund Sangyo K.K.), 100 g of fine crystalline cellulose (Abicel pH 301, manufactured by Asahi Chemical Industry Co., Ltd.), 100 g of sodium carboxymethyl starch and 5 g of magnesium stearate were uniformly mixed and tabletted by a usual method to obtain a tablet drug containing 10 mg of NB-818 per tablet.

EXAMPLE 4

50 g of NB-818, 250 g of lactose and 195 g of s-starch were uniformly mixed, and 60 g of pure water was added thereto. The mixture was granulated and dried, and then the granule size was adjusted. Then, 5 g of magnesium stearate was added, and the mixture was compressed by a usual method to obtain a tablet drug containing 10 mg of NB-818 per tablet.

EXAMPLE 5

40 g of white vaseline was added to a mixture comprising 50 g of heat-melted microcrystalline wax and 100 g of paraffin, and the mixture was kneaded by a pulverizer. A suspension of 10 g of NB-818 in 10 g of isopropyl myristate, was gradually added thereto, and the mixture was kneaded to be uniform, to obtain a ointment.

EXAMPLE 6

10 g of NB-818 finely pulverized to a size of not larger than 100 μm is dispersed and suspended in distilled water for injection having 6 g of sodium carboxymethyl cellulose, 10 g of polyoxyethylene hardened caster oil (HCO-60, manufactured by Nicol K.K.), 2 g of trisodium citrate and 0.3 g of citric acid dissolved, to obtain a suspension type injection solution having a total volume of 600 ml.

EXAMPLE 7

Levo-rotatory optical isomer of 2-carbamoyloxymethyl-4-(2,3-dichlorophenyl)-6-methyl-1,4-dihydropyridine-3,5-dicarboxylic acid 3-isopropyl ester 5-methyl ester 1) Preparation of S-(+)-β-methoxy-2-phenylethanol 3.5 g of S-(+)-β-methoxy-phenylacetic acid (optical purity: 99%, manufactured by Aldrich Co.) was dissolved in 40 ml of diethyl ether. To this solution, 70 ml of a diethyl ether suspension containing 1.05 g of lithium aluminum hydride was gradually dropwise added under stirring and cooling with ice. After completion of the dropwise addition, the mixture was refluxed under heating for one hour and then left to cool to room temperature. Then, 40 ml of 10% sulfuric acid was added under cooling with ice to decompose the excessive reducing agent. The aqueous layer was separated and extracted three times each with 100 ml of diethyl ether. The extracts were combined and washed with 42 ml of 10% sulfuric acid and 100 ml of water. The extract solution thus obtained was dried over anhydrous magnesium sulfate and dried and concentrated under reduced pressure to obtain 31.7 g [[α]$_D^{25}$+116.1° (C=1,280, ethanol) (yield: 98.9%)] of the above identified compound as colorless oil.

2) Preparation of S-(+)-β-methoxy-2-phenethyl acetoacetate 2 g of the alcohol compound obtained in the above step 1 was dissolved in 20 ml of acetone, and 134 mg of triethyl amine was added thereto. Then, 1.5 ml of an acetone solution containing 1.46 g of diketene was added thereto, and the mixture was refluxed under heating for 2 hours. To the reaction solution thus obtained, 9.5 ml of 1N hydrochloric acid and 38 ml of water were added, and the mixture was extracted twice each with 100 ml of methylene chloride. The extracts were put together and dried over anhydrous magnesium sulfate, and then the solvent was distilled off under reduced pressure. The residue was purified by silica gel column chromatography (80 g of Wacogel C-200, eluting solution: hexane/ethyl acetate=2/1) to obtain 2.85 g [[α]$_D^{25}$+69.2° (C=1.053, ethanol) (yield: 91.8%)] of the above identified compound as colorless oil.

3) Preparation of S-(+)-β-methoxyphenethyl 2-(2,3-dichlorobenzylidene)acetoacetate 2.73 g of the ester compound obtained in the above step 2 and 2.43 g of 2,3-dichlorobenzaldehyde were dissolved in 145 ml of benzene. Then, 58 μl of piperidine and 36 μl of acetic acid were added thereto, and the mixture was refluxed under heating for 3 hours. The solvent of the reaction solution thereby obtained was distilled off under reduced pressure, and the residue was purified by silica gel column chromatography (150 g of Wacogel C-200, eluting solvent: hexane/ethyl acetate=1/5) to obtain 3.58 g (yield: 78.7%) of a mixture of geometrical isomers of the above identified compound as yellow oil.

4) Preparation of 2-acetoxymethyl-4-(2,3-dichlorophenyl)-6-methyl-1,4-dihydropyridine-3,5-dicarboxylic acid 3-isopropyl ester 5-(S)-(+)-β-methoxyphenethyl ester 3.0 g of the benzylidene compound obtained in the above step 3 and 1.84 g of isopropyl 4-acetoxy-3-aminocrotonate were dissolved in 120 ml of ethanol, and the mixture was refluxed under heating for 79 hours. The reaction solution thereby obtained was concentrated under reduced pressure. The residue was purified by silica gel column chromatography (150 g of Wacogel C-200, eluting solvent: hexane/acetic acid=2/1) to obtain 3.6 g (yield: 82%) of a mixture of diastereomers of the above identified compound.

The mixture of the diastereomers was separated by fractional liquid chromatography (column: Senshu Pak Silica 5031-N (20φ×30 mm), mobile phase: hexane/ethyl acetate =2/1, detection: UV 254 nm, flow rate: 20 ml/min) to obtain 1.1 g of the desired optical isomer among the diastereomers of the above identified compound, as a post eluting component.

5) Preparation of 2-hydroxymethyl-4-(2,3-dichlorophenyl)-6-methyl-4-dihydropyridine-3,5-dicarboxylic acid 3-isopropyl ester 5-methyl ester 1.01 g of the post eluting component of the diastereomers obtained in the above step 4 was dissolved in 35 ml of a methanol solution of 0.1 mmol sodium methoxide, and the solution was stirred at room temperature for 20 minutes. The reaction solution thereby obtained was neutralized by an addition of five drops of acetic acid and then concentrated under reduced pressure. The residue was extracted by an addition of 50 ml of ethyl acetate and 20 ml of a saturated sodium chloride aqueous solution. The organic layer was separated and dried over anhydrous magnesium sulfate, and the solvent was distilled off under reduced pressure to obtain a residue.

The residue was dissolved in 13 ml of methylene chloride, and 286 μg of pyridine, 338 mg of p-toluene sulfonic acid and 1.3 ml of isopropenyl methyl ether were added thereto. The mixture was stirred at room temperature for one hour. The reaction solution thereby obtained was washed with 5.1 ml of a saturated sodium chloride aqueous solution and then with 5 ml of a 5% sodium carbonate aqueous solution and the dried over anhydrous sodium sulfate. Then, the solvent was distilled off under reduced pressure. The residue thereby obtained was purified by silica gel column chromatography (50 g of Wacogel C-200, eluting solvent: hexane/ethyl acetate=2/1) to obtain 0.88 g (yield: 83%) of 2-[1-(1-methoxy-1-methyl)ethyl]oxymethyl-4-(2,3-dichlorophenyl)- 6-methyl-1,4-dihydropyridine-3,5-dicarboxylic acid 3-isopropyl ester 5-(S)-(+)-β-methoxyphenethyl ester as yellow oil.

0.88 g of the methoxyisopropylether-protected compound thus obtained was added to 70 ml of a 0.13M sodium methoxide solution, and the mixture was refluxed under heating for 30 hours. The reaction solution thereby obtained was left to cool, and then 4 ml of acetic acid was added thereto. The mixture was left to stand at room temperature overnight and then concentrated under reduced pressure. The residue thereby obtained was dissolved in 200 ml of ethyl acetate and then washed with a 5% sodium hydrogen carbonate aqueous solution and dried over anhydrous magnesium sulfate. After removing the solid by filtration, the solvent was distilled off under reduced pressure. The residue was roughly purified by silica gel column chromatography (50 g of Wacogel C-300, eluting solvent: hexane/ethyl acetate=2/1) and then purified by fractional liquid chromatography (column: Senshu Pak Silica 5031-N (20φ×30 mm), mobile phase: hexane/ethyl acetate=1/1, detection: UV 254 nm, flow rate: 20 ml/min) to obtain 0.23 g (yield: 32%) of the above identified compound as colorless oil.

6) Preparation of levo-rotatory optical isomer of 2-carbamoyloxymethyl-4-(2,3-dichlorophenyl)-6-methyl-1,4-dihydropyridine-3,5-dicarboxylic acid 3-isopropyl ester 5-methyl ester 0.22 g of the 2-hydroxymethyl compound obtained in the above step 5 was dissolved in 45 ml of benzene, and 62 μl of chlorosulfonyl isocyanate was added thereto. The mixture was stirred at room temperature for 30 minutes. Then, 6 ml of water was added thereto to decompose the excess chlorosulfonyl isocyanate. Then, the mixture was extracted by an addition of 20 ml of ethyl acetate. The extract solution thereby obtained was washed with 10 ml of a saturated sodium chloride aqueous solution and dried over anhydrous magnesium sulfate. Then, the solvent was distilled off under reduced pressure, and the residue was dissolved in a mixture comprising 1 ml of ethyl acetate and 1 ml of isopropyl ether. Then, 4 ml of hexane was added to the solution, and the mixture was stirred for 4 hours under cooling with ice. Precipitated crystals were collected by filtration and dried under reduced pressure to obtain 0.18 g (yield: 75%) of the above identified compound as colorless needle-like crystals.

mp: 131°–132° C. $[\alpha]_D^{20}$:−52.5° (c=0.958, ethanol) λmax: 236 nm, 360 nm (methanol) IR (KBr) vcm$^{-1}$: 3450, 3400, 3340, 3000, 2950, 1725, 1705, 1665, 1605, 1490, 1385, 1320, 1295, 1280, 1210, 1095, 865, 800, 770, 730 NMR δppm: 0.83–1.40(m,6H), 2.28(s,3H), 3.53(s,3H), 4.63–5.26(m,3H), 5.37(s,1H), 6.66(s,2H), 7.10–7.58(m,3H), 8.83(s,1H)

The effective activities of NB-818 of the present invention for ameliorating cerebral circulation have distinct selectivity for cerebral blood vessels and further have a long effective period which has never been observed with conventional products. For example, as compared with the analogous compounds disclosed in the above-mentioned Japanese Unexamined Patent Publication No. 2373/1984 and with commercially available ameliorants of cerebral circulation such as nicardipine and nimodipine, the compound of the present invention distinctly increases the blood flow of the cerebral blood vessels at a low dose as compared with such comparative drugs, particularly at such a dose as giving no substantial affect to the peripheral (femoral artery) blood flow and the blood pressure. Further, the effective period is significantly superior to that of the comparative drugs. Further, the activities of the compound of the present invention for ameliorating cerebral circulation exhibit preventive and curing effects distinctly superior to the conventional drugs in the experimentally induced cerebral ischemia models and amnesia models, and thus also have the brain protecting effects and the effects to activate the cerebral function and metabolism.

Thus, the ameliorant of cerebral circulation of the present invention is useful as a preventive and curing agent for the blood flow trouble due to a usual defect in the cerebral blood vessels and the accompanying hypoxia, convulsion or forcible want of sleep and consequential troubles in learning or memory, dementia due to old age, or amnesia.

The levo-rotatory optical isomer of NB-818 is excellent in the intensity and the effective period of the vasodilation activities and thus is useful as a hypotensive agent. Further, the activities of the levo-rotatory optical isomer of NB-818 of the present invention are specific to the cerebral blood vessels. Therefore, it is useful also as a curing agent for various cerebral diseases such as cerebral blood vessel troubles, cerebral infarction, cerebral hemorrhage, cerebral contrusion, cerebral ischemia, demensia and defects of memory.

We claim:

1. A method of ameliorating cerebral circulation comprising administering an effective amount of 2-carbamoyloxymethyl-4-(2,3-dichlorophenyl)-6-methyl-1,4-dihydropyridine-3,5-dicarboxylic acid 3-isopropyl ester 5-methyl ester.

2. The method of claim 1, wherein said 2-carbamoyloxymethyl-4-(2,3-dichlorophenyl)-6-methyl-1,4-dihydropyridine-3,5-dicarboxylic acid 3-isopropyl ester 5-methyl ester is administered in a pharmaceutical composition also comprising a pharmaceutically acceptable diluent.

* * * * *